(12) United States Patent
Yokota et al.

(10) Patent No.: US 6,721,048 B2
(45) Date of Patent: Apr. 13, 2004

(54) DETECTOR FOR SPECTROMETRY AND INTEGRATING SPHERE MEASURING DEVICE, AND SPECTROPHOTOMETER USING THE SAME

(75) Inventors: Kazumi Yokota, Osaka-fu (JP); Kaori Kinoshita, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 94 days.

(21) Appl. No.: 09/922,845

(22) Filed: Aug. 7, 2001

(65) Prior Publication Data

US 2002/0024664 A1 Feb. 28, 2002

(30) Foreign Application Priority Data

Aug. 24, 2000 (JP) ........................................ 2000-253469

(51) Int. Cl.$^7$ .................................................. G01J 3/42
(52) U.S. Cl. ........................ 356/319; 356/236; 250/228
(58) Field of Search ................................ 356/319, 236; 250/228

(56) References Cited

U.S. PATENT DOCUMENTS

| 5,084,747 | A | * | 1/1992 | Miyawaki ................. 250/226 |
| 5,125,739 | A | * | 6/1992 | Suarez-Gonzalez et al. 250/226 |
| 5,164,844 | A | * | 11/1992 | Granger ..................... 250/228 |
| 5,422,483 | A | * | 6/1995 | Ando et al. ............. 250/339.02 |
| 6,061,140 | A | * | 5/2000 | Berg et al. ................. 356/418 |
| 6,396,040 | B1 | * | 5/2002 | Hill .......................... 250/205 |

* cited by examiner

Primary Examiner—F. L. Evans
Assistant Examiner—Kara Geisel
(74) Attorney, Agent, or Firm—Kanesaka & Takeuchi

(57) ABSTRACT

In a detector for spectrometry attached to an integrating sphere, a plurality of detection elements having different spectral sensitivity characteristics is arranged side by side in the same plane on a base, and a side cover is provided such that the detection elements receive light. Thus, the measurement light is directly irradiated to the respective detection elements. Accordingly, the detector for spectrometry has a fast response speed and is excellent in the sensitivity characteristics in a wide wavelength region in the near-infrared area.

8 Claims, 2 Drawing Sheets

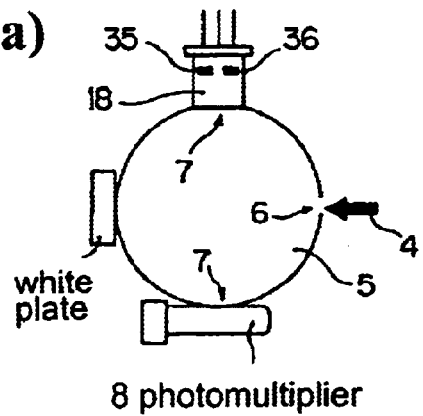
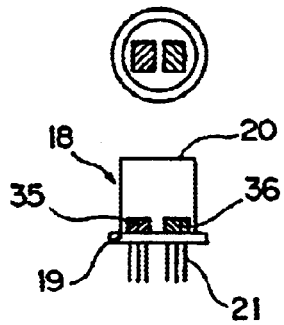
Fig. 1(a)
Fig. 1(b)
Fig. 1(c)
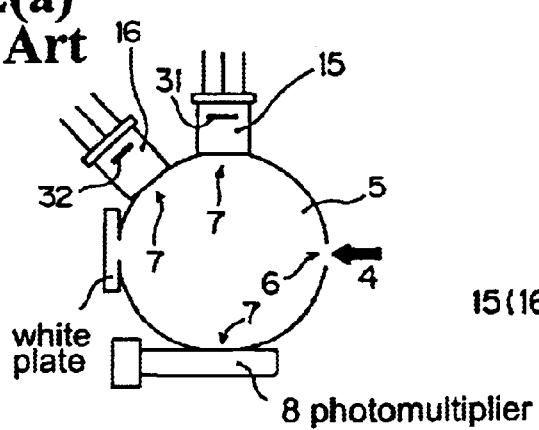
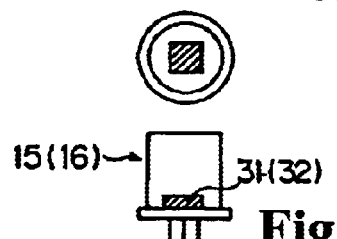
Fig. 2(a) Prior Art
Fig. 2(b) Prior Art
Fig. 2(c) Prior Art
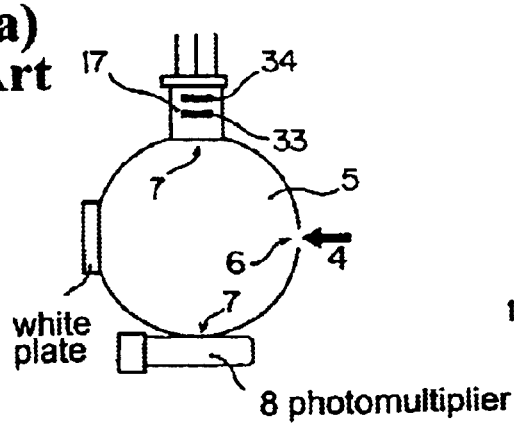
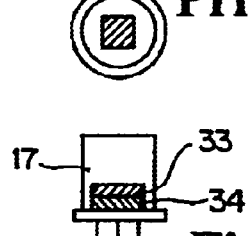
Fig. 3(a) Prior Art
Fig. 3(b) Prior Art
Fig. 3(c) Prior Art

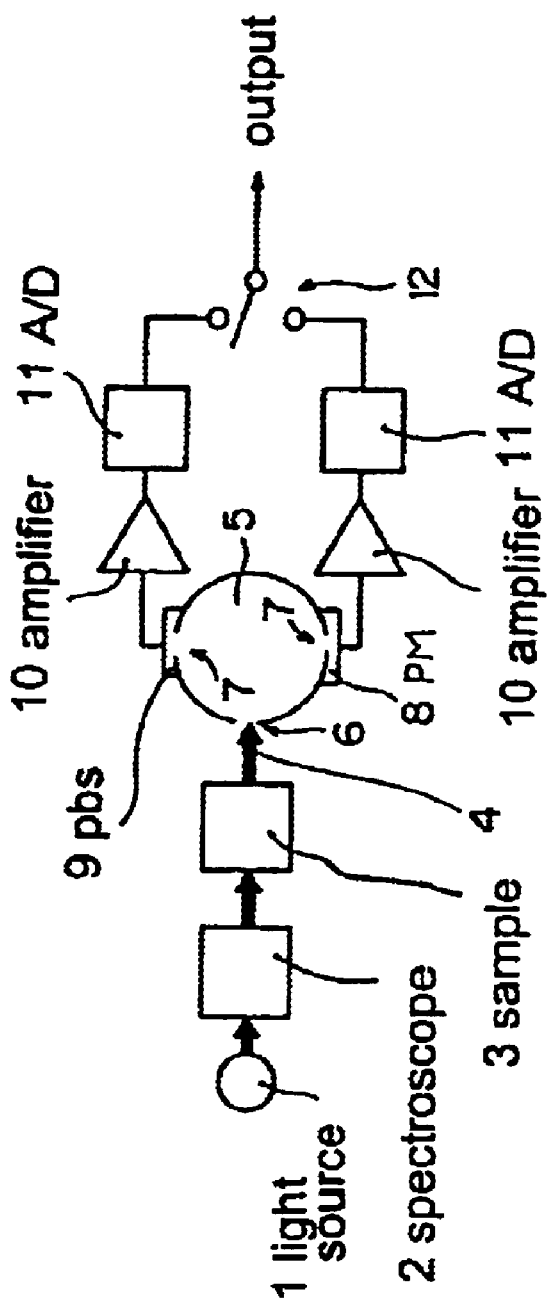

DETECTOR FOR SPECTROMETRY AND INTEGRATING SPHERE MEASURING DEVICE, AND SPECTROPHOTOMETER USING THE SAME

BACKGROUND OF THE INVENTION AND RELATED ART STATEMENT

The present invention relates to a detector used for spectrometry, and especially, to a detector which is suitable for measuring a wide wavelength region by using an integrating sphere with a high sensitivity at high response speed. Also, the present invention relates to a spectrophotometer which conducts a measurement by using the integrating sphere.

Conventionally, as one method for spectrometry, a measurement using an integrating sphere has been carried out. In case the spectrometry is conducted in a wide wavelength region by using the integrating sphere, two or more detectors which are respectively suitable for a short wavelength area and a long wavelength area are attached to the integrating sphere. As a combination of these detectors, a photomultiplier (PM) used for the short wavelength side and a PbS detector (PbS) used for the long wavelength side have been well known.

FIG. 4 shows a structure of a conventional spectrophotometer in case transmittance is measured by using an integrating sphere. In the figure, numeral 1 designates a light source; numeral 2 designates a spectroscope for dividing a light from the light source into respective wavelengths; numeral 3 designates a sample to which the divided light is irradiated to carry out a measurement of transmittance; and numeral 4 designates a sample light which is transmitted through the sample. The sample light is led to an integrating sphere 5.

In the integrating sphere 5, there are formed an entrance window 6 for leading the sample light 4 to an inside of the integrating sphere 5, and light outgoing windows 7 for leading the light scattered in multiple in the integrating sphere to a photomultiplier (PM) and a PbS detector (PbS). Numeral 8 designates the photomultiplier (PM) attached to one of the light outgoing windows, and numeral 9 designates the PbS detector (PbS) attached to the other light outgoing window. Numeral 10 designates an amplifier which amplifies a detected signal from the photomultiplier (PM) or the PbS detector (PbS), numeral 11 designates an analog-to-digital converter, and numeral 12 designates a change-over switch for switching to determine which one of the signals from the detectors is outputted to outside.

When the sample light 4 is introduced into the integrating sphere 5 from the light incoming window 6, the light is subjected to the multiple scattering to reach the light outgoing window 7. When the scattered light is received at the photomultiplier 8 or PbS detector 9, the light is detected, and outputted to outside (a personal computer for data processing connected in a subsequent stage) via the amplifier 10 and analog-to-digital converter 11. Then, by switching the change-over switch 12 in accordance with the measured wavelength area, a signal from one of the detectors is sent out.

In the aforementioned detectors, the PbS detector 9 is used as a detector for a near-infrared region. Although the PbS detector 9 is advantageous in that the PbS detector can be used in a wide wavelength range of the near-infrared region, the spectral sensitivity characteristic of the PbS detector is inferior to that of a near-infrared detector using other semiconductor elements. Also, a response speed of the PbS detector is relatively slow. Therefore, the PbS detector is not suitable for a measurement with the high response speed.

Thus, in order to improve the sensitivity in the near-infrared region, or in order to conduct the measurement with the high response speed, it is necessary to use a detector other than the PbS detector. However, so far, there is no appropriate detector which has a high spectral sensitivity characteristic throughout the wide wavelength range in the near-infrared region and which can be used in the spectrophotometer. Thus, in order to carry out the measurement for the wide wavelength range of the near-infrared with the high sensitivity, it is necessary to attach two or more near-infrared detectors having different spectral sensitivity characteristics to the integrating sphere, wherein these detectors are switched in use.

FIGS. 2(a)–2(c) show an integrating sphere provided with two near-infrared detectors. In FIGS. 2(a)–2(c), the components which are the same as those in FIG. 4 are designated by the same numeral references, so that explanations therefor are omitted herewith. In the integrating sphere 5, as detectors for the near-infrared region, a first detector 15 and a second detector 16 are respectively attached to the light outgoing windows 7.

In the first detector 15, there is attached a first semiconductor element 31 having a high sensitivity range in a relatively shorter wavelength side among the near-infrared, and in the second detector 16, there is attached a second semiconductor element 32 having a high sensitivity range in a wavelength side longer than that of the semiconductor element used in the first detector. As a combination of these elements, there can be considered a combination in which Si (silicon) is used in the first semiconductor element, and InGaAs is used in the second semiconductor element. Also, as another example, there can be considered a combination in which InGaAs is used both in the first semiconductor 31 and the second semiconductor 32, but high sensitivity wavelength ranges of these semiconductor elements are different by changing the composition ratio thereof.

The device shown in FIGS. 2(a)–2(c) is excellent in the response speed and sensitivity. However, it is necessary to provide two light outgoing windows for the near-infrared region in the integrating sphere. Since a performance of the integrating sphere becomes better as an area occupied by the windows as opening sections becomes smaller, if the number of the windows is increased, the performance of the integrating sphere is deteriorated. Of course, if the area of each window can be reduced, the above problem might be solved. However, since packages of the detectors are required to be attached to the windows to lead the measurement light to the detector, there is a limit to reduce each of the areas of the windows. Thus, in order to increase the performance of the integrating sphere, it is necessary to reduce the number of the light outgoing windows, and it is also necessary to have only one near-infrared detector.

Therefore, as shown in FIGS. 3(a)–3(c), it is considered to use a transmission type compound detector 17 as a detector. The transmission type compound detector 17 has a laminate structure in which a first semiconductor detection element 33 and a second semiconductor detection element 34 are laminated, and a light in the same optical path can be detected by the two different kinds of the detection elements. For example, a transmission type compound detector has been available on the market, wherein Si (silicon) is used as the first semiconductor element and Ge or InGaAs are used as the second semiconductor element.

In this type of the detector, since optical paths of the two elements are the same, only light transmitted through the first semiconductor detection element in a front side reaches the second semiconductor detection element in a rear side. Namely, regarding the detection element in the rear side, even in case light in a range of wavelengths for which the spectral sensitivity characteristic of the rear detection element is good is irradiated, if the light with the wavelengths is absorbed at the detection element in the front side, the light reaches the detection element in the rear side after loss in a quantity of light occurs at the front side, resulting in that the measurement with high sensitivity is difficult. In other words, when the maximum sensitivity wavelengths of both detection elements are close to each other, the loss in quantity of the light reaching the second semiconductor detection element occurs, so that the effective measurement can not be carried out.

Therefore, in order to effectively use the transmission type compound detector, it is necessary that the maximum sensitivity wavelengths of the detection elements are different and away from each other. When the two detection elements having the maximum sensitivity wavelengths extremely away from each other are combined, consequentially, a low sensitivity region appears in an intermediate wavelength range between the maximum sensitivity wavelengths of the detection elements. Therefore, even if the transmission type compound detector is used, it is difficult to carry out the high sensitivity measurement in the wide wavelength range of the near-infrared region.

As described above, due to the structure of the conventional detector, it is difficult to carry out the high sensitivity measurement while the performance of the integrating sphere is maintained, that is, without increasing the number of the windows in the integrating sphere.

Accordingly, an object of the invention is to provide a detector for spectrometry and an integrating sphere measurement device using the detector, in which a structure of the detector is contrived to enable the high sensitivity measurement while the performance of the integrating sphere is maintained.

Further objects and advantages of the invention will be apparent from the following description of the invention.

SUMMARY OF THE INVENTION

To achieve the aforementioned object, the present invention provides a detector for spectrometry, in which a plurality of detection elements having different spectral sensitivity characteristics is arranged in a planar direction, i.e. side by side, on a base as a light receiving surface, and stored in one package including a light receiving window.

As the detection elements having different spectral sensitivity characteristics used in the detector, semiconductor detection elements are suitable since the semiconductor detection elements have a high response speed and an excellent sensitivity characteristic even in a small area. As a combination of the semiconductor detection elements, there can be a combination of semiconductor detection elements in which semiconductor materials themselves are different, or a combination of semiconductor detection elements in which the semiconductor materials are the same but the composition ratios thereof are different.

Incidentally, although a detector, such as a photodiode array detector (PDA), in which a plurality of detection elements having the same spectral sensitivity characteristics is arranged on the plane, is available on the market, this kind of the detector is not included in the detector of the invention. In the first place, the PDA is used for the purpose of measuring a spatial (positional) distribution of quantity of light, and is not provided for detecting light in a single optical path, such as light from a light outgoing window of the integrating sphere.

Two or more detection elements are arranged side by side on the plane of the base, and in order to shield the unnecessary light from the outside and guide only the sample light from one direction to the base as the light receiving surface, the detection elements are stored in a package. Since any detection elements can directly receive the sample light by arranging the detection elements in the plane, there is no problem that the quantity of light is lost at the detection element in the rear side of the transmission type compound detector as shown in FIG. 3(a).

Further, the detector for spectrometry described above is attached to one light outgoing window of the integrating sphere, and only the measurement light from the light outgoing window of the integrating sphere is directly irradiated to the respective two or more detection elements placed on the base.

Therefore, when the sample light enters into the integrating sphere from the light incoming window of the integrating sphere, multiple scattering of the light occurs in the integrating sphere, and the light is irradiated from the light outgoing window to the respective detection elements and converted into electric signals to issue detection signals. Thus, by selecting the signal from the appropriate detection element in accordance with the measured wavelength area to take out the same, the spectrometry with the high sensitivity using the integrating sphere can be carried out.

BRIEF DESCRIPTION OF THE DRAWINGS

FIG. 1(a) is an explanatory view showing a structure of an integrating sphere measuring device as an embodiment of the invention and a structure of a detector for spectrometry used therein; FIG. 1(b) is a plan view of the detector; and FIG. 1(c) is a front view of the detector;

FIG. 2(a) is an explanatory view showing a structure of a conventional integrating sphere measuring device and a conventional detector for spectrometry used therein; FIG. 2(b) is a plan view of the detector; and FIG. 2(c) is a front view of the detector;

FIG. 3(a) is an explanatory view showing a structure of another conventional integrating sphere measuring device and a conventional detector for spectrometry used therein; FIG. 3(b) is a plan view of the detector; and FIG. 3(c) is a front view of the detector; and FIG. 4 is an explanatory view showing an entire structure of a spectrophotometer using an integrating sphere.

DETAILED DESCRIPTION OF PREFERRED EMBODIMENTS

Hereunder, an embodiment of the invention will be explained with reference to the attached drawing. FIG. 1(a) is a view showing a structure of an integrating sphere measuring device as an embodiment of the invention and a structure of a detector for spectrometry attached to the integrating sphere measuring device.

Firstly, the structure of the detector for spectrometry will be explained. In a detector 18 for spectrometry shown in a plan view in FIG. 1(b) and a front view in FIG. 1(c), a first semiconductor detection element 35 and a second semiconductor detection element 36 are placed on an upper surface of a base 19 in a disc shape. These two semiconductor detection elements have different spectral sensitivity characteristics. For example, Si (silicon) having the sensitivity characteristic in a shorter wavelength side among the near-infrared is used for the first semiconductor detection element 35, and InGaAs having the spectral sensitivity characteristic in a wavelength side longer than that of Si is used as the second semiconductor detection element 36. Alternatively, since the spectral sensitivity characteristics of the semiconductor detection element, such as InGaAs, are changed in accordance with the composition ratio thereof, the semiconductors of the same material which have different composition ratios may be used.

For example, first InGaAs having the spectral sensitivity characteristic in wavelengths of 0.9 to 1.7 $\mu$m can be used as the first semiconductor detection element 35, and second InGaAs having the spectral sensitivity characteristic in wavelengths of 1.2 to 2.6 $\mu$m can be used as the second semiconductor detection element 36. As described above, it is preferable to use two kinds of detection elements having the spectral sensitivity characteristics in which the maximum sensitivity wavelengths are close to each other and sensitivity regions thereof are partially overlapped. If the sensitivity regions are completely separated, the combined sensitivity characteristic has a concave and a convex to have a region with the low sensitivity in an intermediate portion, so that a quantitative measurement becomes difficult.

Necessary lead wires 21 including anode and cathode are attached from the first semiconductor detection element 35 and the second semiconductor detection element 36 such that the lead wires 21 pass through the base 19 to extend from the lower side. Other than the anode and cathode, lead wires including an earth wire for a body, a wire for a cooling element in case the cooling element is provided, and a wire for a temperature measuring element in case a temperature of the cooling element is measured may pass through the base 19.

Also, a side cover 20 in a cylindrical shape is attached on the upper surface of the base 19 such that the side cover 20 surrounds the first semiconductor detection element 35 and the second semiconductor detection element 36, and the first semiconductor detection element 35 and the second semiconductor detection element 36 are packed by the base 19 and the side cover 20. Accordingly, a stray light from a side direction is shielded or blocked, and only the light from the upper side as a light receiving window of the detector reaches the semiconductor detection elements 35 and 36.

Incidentally, the package for the first semiconductor detection element 35 and the second semiconductor element 36 are not limited to the side cover in the cylindrical form described above. The shape of the package can be any shape as long as the package is structured to have the light incoming window through which light from a specific direction is only introduced such that the light entered from the light incoming window is directly and equally irradiated to a plurality of detection elements disposed in a plane.

Next, explanation is made for an integrating sphere measuring device to which the detector 18 for spectrometry described above is attached. In the integrating sphere measuring device shown in FIG. 1(a), the detector is attached to an integrating sphere 5 (integrating sphere main body). In the integrating sphere 5, there are formed a light incoming window 6 through which sample light 4 is introduced, and two light outgoing windows 7 through which measurement lights after the multiple scattering reflection in the integrating sphere 5 are ejected. The photomultiplier 8 and the detector 18 for the spectrometry are attached by positioning the same to the light outgoing windows 7.

In the present invention, the integrating sphere 5 is provided with only one light outgoing window 7 other than the light outgoing window 7 to be attached to the photomultiplier 8, and a number of the detector for spectrometry attached to a portion other than the photomultiplier 8 and used for measurement of a near-infrared region is only one. By decreasing the number of the light outgoing windows, an effective reflection area of an inner wall of the integrating sphere is increased as much as possible.

Incidentally, although detailed explanations are omitted since it is not so relevant to the present invention, a window for reflectivity measurement is formed on a side opposite to the light incoming window 6, where the light introduced from the light incoming window 6 is reflected first in the integrating sphere 5. In case of conducting the reflectivity measurement, a sample for the reflectivity measurement is attached to the aforementioned position. In case of a transmittance measurement, a reference white board is attached to this position. Needless to say, it is preferable that the window for reflectivity measurement is not provided in case the reflectivity measurement is not conducted and only the transmittance measurement is conducted.

In an entire structure of a spectrophotometer using the integrating sphere, the detector 18 for the spectrometry described above is attached to the structure shown in FIG. 4 instead of the PbS detector 9. Then, the lead wires 21 from the first semiconductor element 35 and the second semiconductor element 36 are respectively connected to the amplifier 10 and the analog-to-digital converter 11, and the change-over switch 12 can switch three signals, which are two signals from the two semiconductor elements, and a signal from the photomultiplier 8.

Incidentally, although FIG. 4 shows a single beam spectrophotometer, it is needles to say that the present invention can be used similarly in a double beam spectrophotometer. Incidentally, although the detector for the spectrometry of the invention is mainly used for the integrating sphere measurement, it is not limited to the case in which the detector is attached to the light outgoing window of the integrating sphere, and the detector for the spectrometry can be applied in case of conducting a measurement of a near-infrared region regarding the measurement light leaking from a small hole as in the light outgoing window of the integrating sphere.

Embodiments of the present invention are summarized, as follows:

(1) a detector for spectrometry or detector for integrating sphere measurement, wherein a semiconductor detection element having Si (silicon) as a base material and a semiconductor detection element having InGaAs as base materials are arranged in a plane on a base as a light receiving surface, and these semiconductor detection elements are stored in one package;

(2) a detector for spectrometry or detector for integrating sphere measurement, wherein a plurality of InGaAs semiconductor detection elements having different spectral sensitivity characteristics due to the difference in the composition ratios is arranged in a plane on a base as a light receiving surface, and these semiconductor detection elements are stored in one package;

(3) a detector for spectrometry or detector for integrating sphere measurement, wherein a plurality of semiconductor detection elements having different spectral sensitivity characteristics is arranged in a plane on a base as a light receiving surface, and a cover is attached to store the elements in one package such that the light only from a predetermined direction is received by these elements; and (4) an integrating sphere measuring device, wherein the detector for integrating sphere measurement described in the above (1), (2) or (3) is attached to one of the light outgoing windows in the integrating sphere.

According to the present invention, since the detector for spectrometry, in which a plurality of detection elements having different spectral sensitivity characteristics is attached in one package, is used, it is possible to carry out a measurement in a wider wavelength range as compared to the case of measuring the near-infrared region by using one detection element. Moreover, since there is no problem of loss in quantity of light which used to occur in the conventional transmission type compound detector, the signal-to-noise ratio can be improved. Also, in case a selection of a combination of the detection elements having different spectral sensitivity characteristics is considered, the combination can be freely selected without considering the overlap of the sensitivity characteristics.

Also, without increasing the number of the light outgoing windows in the integrating sphere in case of attaching the detector to the integrating sphere, the detection elements can be increased, so that the performance of the integration sphere measuring device can be improved.

Further, as compared with the case using the PbS detector, the sensitivity in the near-infrared region can be improved, and at the same time, the response speed can be improved.

While the invention has been explained with reference to the specific embodiments of the invention, the explanation is illustrative and the invention is limited only by the appended claims.

What is claimed is:

1. A detector for spectrometry, comprising:
    a package having a light receiving window and a base as a light receiving surface, and
    a plurality of detection elements having different spectral sensitivity characteristics, said plurality of detection elements being arranged side by side on the base to be stored in the package and being switched in accordance with a measured wavelength range.

2. A detector for spectrometry according to claim 1, wherein said package includes a cover attached to the base.

3. A detector for spectrometry according to claim 1, wherein said detection elements are formed of different base materials to have the different spectral sensitivity characteristics.

4. A detector for spectrometry according to claim 1, wherein said detection elements are formed of same base materials having different composition ratios to have the different spectral sensitivity characteristics.

5. A detector for spectrometry according to claim 1, wherein said plurality of detection elements arranged side by side is disposed to directly face the light receiving window.

6. An integrating sphere measuring device, comprising:
    a detector for spectrometry including a package having a light receiving window and a base as a light receiving surface, and a plurality of detection elements having different spectral sensitivity characteristics, said plurality of detection elements being arranged side by side on the base to be stored in the package and being switched in accordance with a measured wavelength range, and
    an integrating sphere having a light outgoing window through which a light is ejected outside the integrating sphere, said detector being attached to the light outgoing window.

7. An integrating sphere measuring device according to claim 6, wherein said plurality of detection elements arranged side by side is disposed to directly face the light receiving window.

8. A spectrophotometer, comprising:
    an integrating sphere,
    a detector to be attached to the integrating sphere as an integrating sphere measuring device, and including a plurality of detection elements having different spectral characteristics, said detection elements being switched in accordance with a measured wavelength range, and
    a package fixed to the integrating sphere and having a light receiving window for receiving light from the integrating sphere and a base as a light receiving surface, said detection elements being arranged side by side on the base and stored in the package.

* * * * *